(12) United States Patent
Delphis

(10) Patent No.: US 6,284,900 B1
(45) Date of Patent: *Sep. 4, 2001

(54) CIS-ISOAMBRETTOLIDE OF HIGH DEGREE OF ISOMER PURITY AND USE THEREOF

(75) Inventor: Claude Delphis, Les Ulis (FR)

(73) Assignee: Synarome, Chartres (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/636,405

(22) Filed: Aug. 10, 2000

Related U.S. Application Data

(60) Continuation-in-part of application No. 09/572,242, filed on May 17, 2000, which is a division of application No. 09/250,645, filed on Feb. 16, 1999.

(51) Int. Cl.[7] .................................................. C07D 313/00
(52) U.S. Cl. ............................................................. 549/346
(58) Field of Search ................................................ 549/346

(56) References Cited

U.S. PATENT DOCUMENTS 4,014,902   3/1977   Tseng ................................ 260/340.9

OTHER PUBLICATIONS

Chemical Abstracts, vol. 98, No. 13, 1983 "Synthesis of Trans Delta9–Isoambrettolide" Majee et al., p. 578.

*Primary Examiner*—Amelia Owens
(74) *Attorney, Agent, or Firm*—Perman & Green, LLP

(57) ABSTRACT

The invention relates to a molecule which is of important olfactory interest for perfumers.

This molecule, i.e. the cis-isoambrettoide, which has a high degree of isomer purity belongs to the group of macrocyclic lactones with a musk odor.

The invention also relates to its use as a fragrance.

11 Claims, 3 Drawing Sheets

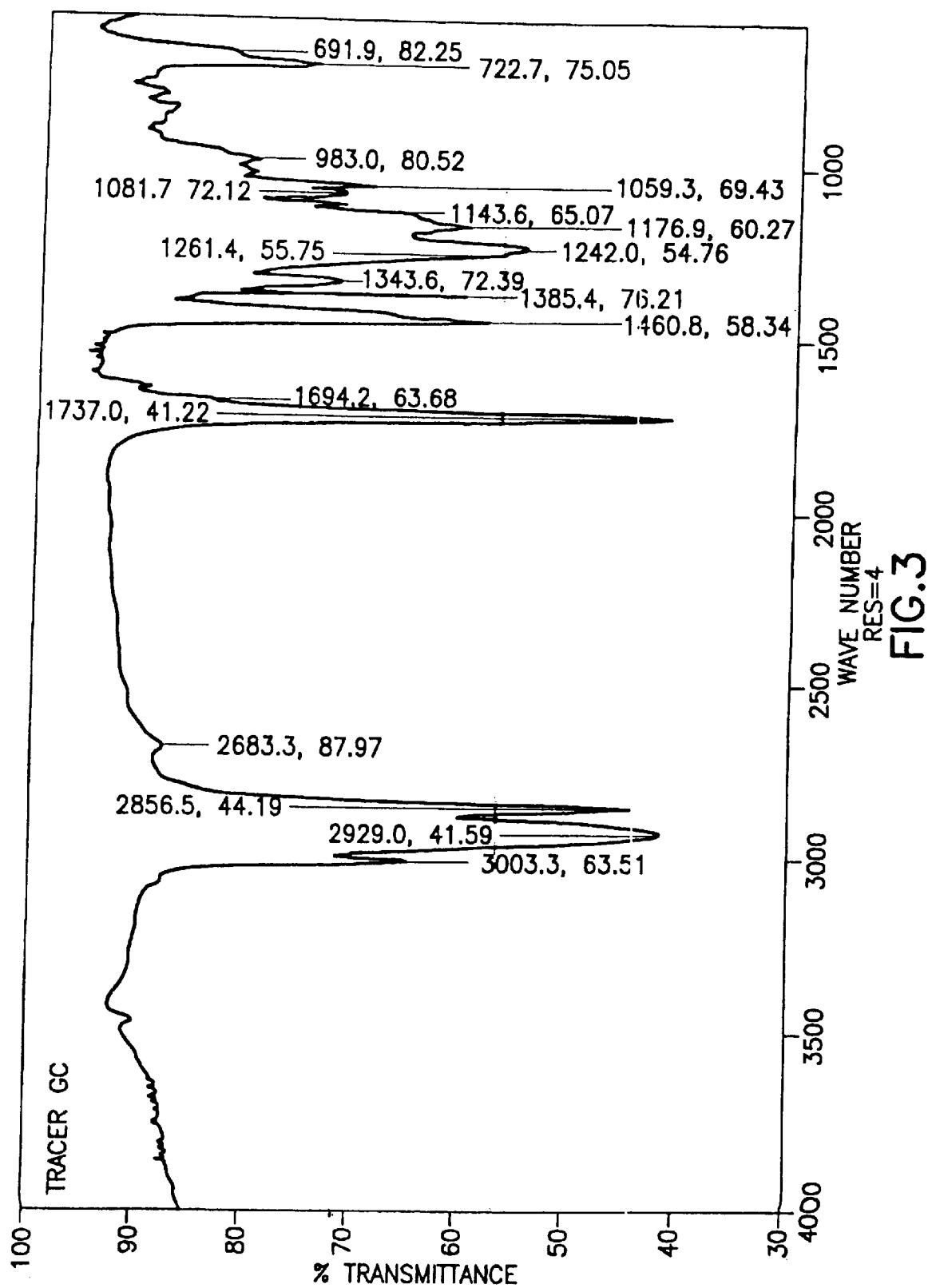

US 6,284,900 B1

CIS-ISOAMBRETTOLIDE OF HIGH DEGREE OF ISOMER PURITY AND USE THEREOF

This application is a continuation-in-part of application Ser. No. 09/572,242, filed May 17, 2000 which in turn is a divisional of application Ser. No 09/250,645, filed Feb. 16, 1999.

BACKGROUND OF THE INVENTION

1. Field of the Invention

The present invention relates to a cis-isoambrettolide in a very high degree of isomer purity and the use thereof.

2. Description of Related Art

It is known that substances with a musk odor are commonly used in the perfume industry in the broad sense, where they have a primary advantage, both in the perfumes sector and in that of washing products such as soaps and detergents, on account of their persistent effect.

These molecules are represented by 4 families: the non-nitro aromatic musks, the nitro aromatic musks, the macrocyclic ketones and the macrocyclic lactones. The lactones are important aromatic agents on account of their abundance in natural products.

Among the macrocyclic lactones of natural origin, derived from the plant kingdom, mention may be made of exaltolide, of formula (1) and ambrettolide, of formula (2).

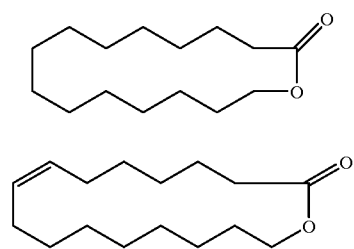

Ambrettolide is obtained from the essential oil and the resinoids of ambrette, whose round, warm, musk note is highly appreciated in perfumery. This plant is Hibiscus abelmoschus 4, which is grown in South America, Indonesia and the West Indies.

An unsaturated macrocyclic lactone is already known: trans-isoambrettolide of formula (3), which is obtained industrially, this being a geometrical and positional isomer of natural ambrettolide. A process for obtaining the trans lactone is described in U.S. Pat. No. 4,014,902.

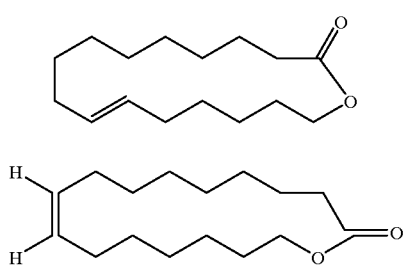

SUMMARY OF THE INVENTION

The present invention relates, however, to an another geometrical and positional isomer of natural ambrettolide: cis-isoambrettolide of formula (4), which has the advantage of being much more powerful than trans-isoambrettolide in olfactory terms, thereby allowing it to be used in the perfume industry at much lower concentrations, resulting in considerable savings which make it all the more appreciated.

In addition, the advantage of the present invention lies in the fact that the cis-isoambrettolide used has a geometrical isomer purity of at least 90%, more preferably about 95% and most preferably at least greater than 97%.

BRIEF DESCRIPTION OF THE DRAWINGS

Reference may be made at this point to the attached figures, in which:

FIG. 3 represents the IR spectrum of cis-isoambrettolide.

DETAILED DESCRIPTION OF THE INVENTION

Figure 1:
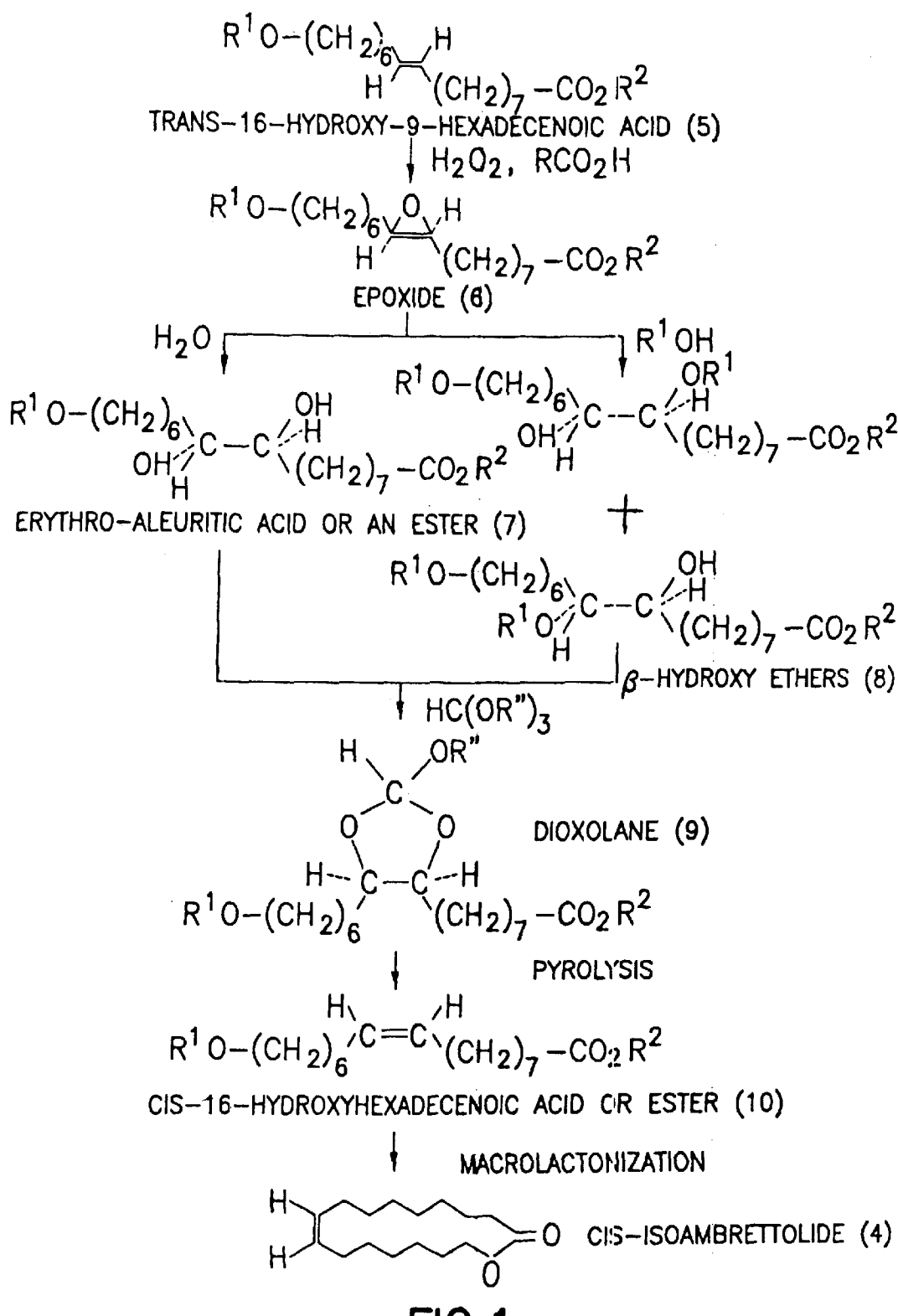
FIG. 1 represents the various steps in the process for manufacturing cis-isoambrettolide.

Cis-16-hydroxy-9-hexadecenoic acid is an essential chemical compound as a starting material for the synthesis of the macrocyclic lactone cis-isoambrettolide, of which it is the direct precursor.

After manufacturing cis-16-hydroxy-9-hexadecenoic acid, cis-isoambrettolide is obtained by the usual macrolactonization methods.

The process for manufacturing cis-isoambrettolide uses the following chemical reaction steps:

a) trans-epoxidation of trans-16-hydroxy-9hexadecenoic acid, of formula (5), which may or may not be esterified, to give the epoxide of formula (6);

b) opening of the epoxide bridge, to give erythro-aleuritic acid, or an ester of this acid, of formula (7);

c) action of an ortho ester of formula $HC(OR'')_3$ on erythro-aleuritic acid, or its ester, to give the dioxolane of formula (9);

d) pyrolysis of the dioxolane to give cis-16-hydroxy-9-hexadecenoic acid, or an ester of this acid, of formula (10), in a purity of greater than 99%;

e) macrolactonization of the above acid, or its ester, resulting in cis-isoambrettolide.

Another process for manufacturing cis-isoambrettolide uses the following chemical reaction steps :

a) trans-epoxidation of trans-16-hydroxy-9-hexadecenoic acid, of formula (5), which may or may not be esterified, to give the epoxide of formula (6);

b) opening of the epoxide bridge to give a mixture of β-hydroxy ethers of formula (8);

c) action of an ortho ester of formula $HC(OR'')_3$ on the mixture of β-hydroxy ethers, to give the dioxolane of formula (9);

d) pyrolysis of the dioxolane to give cis-16-hydroxy-9-hexadecenoic acid, or an ester of this acid, of formula (10), in a purity of greater than 99%;

e) macrolactonization of the above acid, or its ester, resulting in cis-isoambrettolide.

In the above formulae:

$R^1$ represents a hydrogen atom or an acetyl radical, $R^2$ represents a hydrogen atom or a methyl radical, R represents a hydrogen atom or a methyl radical, R' represents a methyl radical or an ethyl radical, R" represents a methyl radical or an ethyl radical.

The examples which follow, which are given as guides, of one embodiment will further illustrate the process for manufacturing cis-isoambrettolide according to the invention, without, however, limiting its scope.

The steps for preparing cis-16-hydroxy-9-hexadecenoic acid, the direct precursor of cis-isoambrettolide, are as follows:

a) preparation of the epoxide of formula (6) from trans-16-hydroxy-9-hexadecenoic acid, which may or may not be esterified, of formula (5), which is treated with hydrogen peroxide in a carboxylic acid medium such as formic acid or acetic acid, to give, via trans-epoxidation, the epoxide of formula (6);

b) opening of the epoxide bridge, by in situ hydrolysis, in acid or basic medium, of the epoxide, to give erythro-aleuritic acid or an ester of this acid, of formula (7);

b') as a variant, opening of the epoxide bridge, by alcoholysis of the epoxide, which gives a mixture of β-hydroxy ethers of formula (8);

c) production of the dioxolane of formula (9) by the action of an ortho ester of formula HC(OR")$_3$, on erythro-aleuritic acid or its ester;

c') as a variant, production of the dioxolane by the action of an ortho ester of formula HC(OR")$_3$ on the mixture of β-hydroxy ethers;

d) production of cis-16-hydroxy-9-hexadecenoic acid or its ester, of formula (10), by pyrolysis, in the presence or absence of solvent, of the dioxolane.

Cis-isoambrettolide is finally obtained by macrolactonization of its precursor acid.

EXAMPLE 1—Production of Cis-isoambrettolide a) Preparation of Erythro-aleuritic Acid 350 ml of 30% hydrogen peroxide and 280 ml of formic acid are loaded into a 2-litre reactor fitted with a stirrer and an external condenser. The temperature of the mixture is lowered to 0° C.

500 g of trans-16-hydroxy-9-hexadecenoic acid are then added, at a rate such that the temperature of the mixture does not exceed 5° C. The temperature is then adjusted to 10° C. The mixture is kept stirring until total conversion, as indicated by chromatography, of the alkene.

The mixture is then diluted with 1 litre of water. It is then left to return to room temperature and stirring is continued for an additional day.

An acid-base extraction of the erythro-aleuritic acid is then carried out. Finally, this acid is purified by crystallization.

It will be noted that if an erythro-aleuritic acid ester is obtained, it will be purified by distillation.

b) Preparation of 16-hydroxyhexadecenoic Acid

The acid or ester obtained above is treated at reflux with an ortho ester, which may be trimethyl orthoformate or triethyl orthoformate, until total conversion is obtained, as indicated by chromatography.

The in situ pyrolysis of the dioxolane thus obtained is then carried out, in the presence or absence of a solvent, which may be toluene or xylene, by raising the temperature to 160° C.

The ω-hydroxy acid or the ω-hydroxy ester thus obtained (cis-16-hydroxy-9-hexadecenoic acid or an ester of the said acid) is purified by distillation.

c) Production of Cis-isoambrettolide

The acid, or its ester, obtained above is treated under the usual macrolactonization conditions, to give cis-isoambrettolide.

The set of steps in the manufacturing process is represented in FIG. 1.

Figure 2:
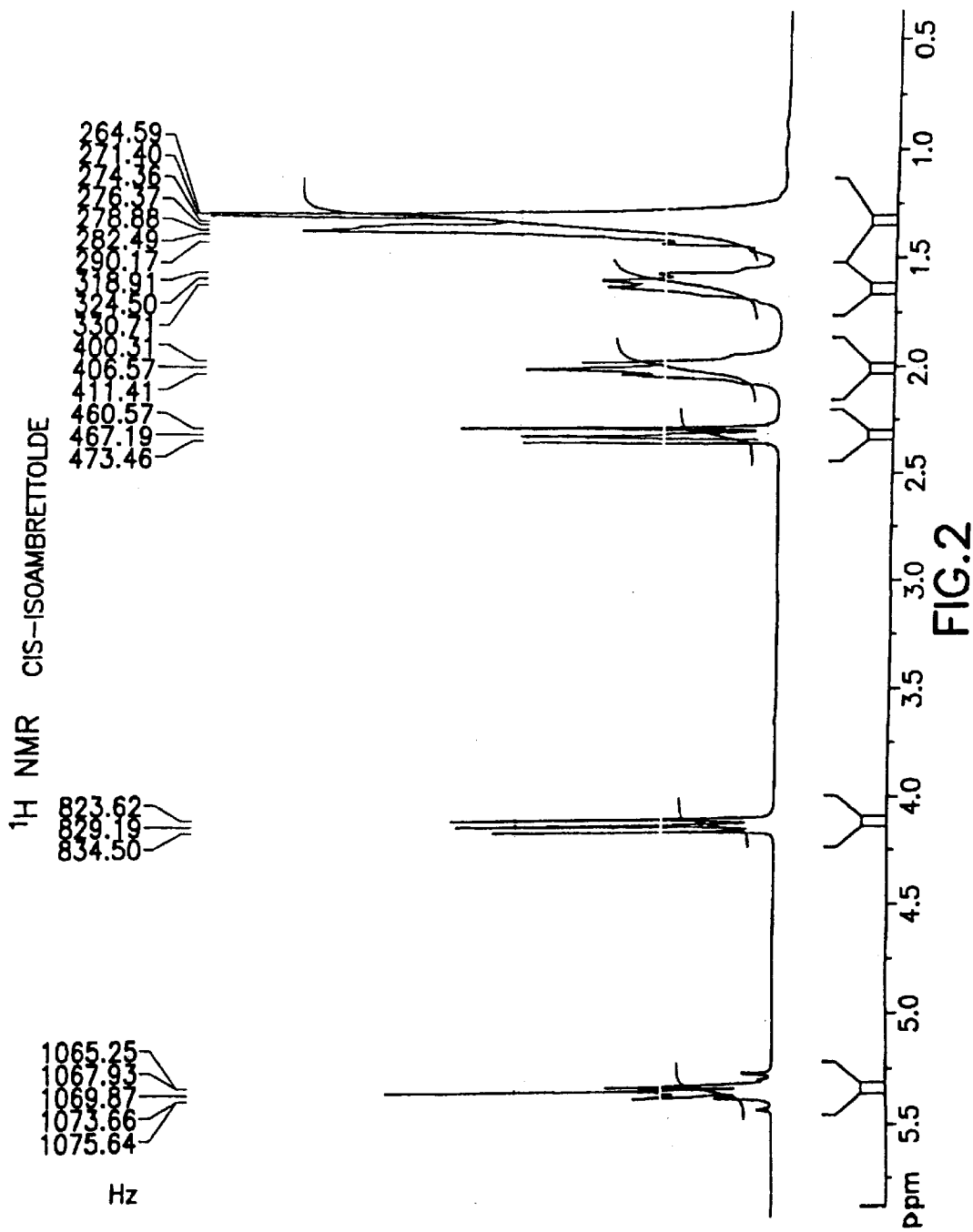
FIG. 2 represents the $^1H$ NMR spectrum of cis-isoambrettolide.

The structure of the cis-isoambrettolide was confirmed by proton nuclear magnetic resonance spectro-scopy and by infrared spectroscopy, as can be seen in FIGS. 2 and 3 respectively, the results of which are given below:

$^1$H NMR analysis of cis-isoambrettolide—solvent: CDCl$_3$

| H | δ (ppm) | integration | |
|---|---------|-------------|---|
| Ha | 5.34 | 2 | Ha-Ha coupling: 8.06 Hz |
| Hb | 4.12 | 2 | |
| Hc | 2.34 | 2 | |
| Hd | 2.03 | 4 | |
| He | 1.34 to 1.6 | 18 | |

Analysis of the Infrared Absorption Spectrum

The significant absorption bands are at about: 2929 cm$^{-1}$; 2883 cm$^{-1}$; 1737 cm$^{-1}$ and 1460 cm$^{-1}$ The round, musk, highly extended note of cis-isoambrettolide makes it a highly advantageous starting material in perfumery.

It gives any perfumery composition the development of the note, its diffusion, its roundness and its long lasting nature without denaturing the note as a whole.

The olfactory effect of the cis-isoambrettolide is perceptible from very low doses, from about 0.01% w/w in a fragrance composition.

Depending on the desired olfactory effect, the common used content of cis-isoambrettolide is from 0.15% to 15% w/w in a fragrance composition.

But it is also conceivable to use a fragrance composition containing only cis-isoambrettolide in order to cover very strong and/or bad odors for example.

A number of examples of compositions for perfumes or perfumed articles such as eaux de toilette, creams, lotions, soaps, detergents and aerosols using cis-isoambrettolide will be found below.

EXAMPLE 1

Thus, it is used in a floral feminine note of jasmine, violet, ylang nature according to the formula below: (parts by weight)

| | |
|---|---|
| Benzyl acetate | 6.00 |
| Styrallyl acetate | 0.50 |
| Cinnamyl alcohol | 1.20 |
| Phenylethyl alcohol | 16.00 |
| Undecylenic aldehyde at 10% | 1.30 |
| Hexylcinnamic aldehyde | 3.50 |
| Defurocoumarinized bergamot | 2.50 |
| Citronellol | 0.80 |
| Eugenol | 0.50 |

-continued

| | |
|---|---|
| Hedione | 0.70 |
| Hydroxycitronellal | 4.00 |
| Ionone 100% | 1.00 |
| Irisarome | 7.00 |
| Isobornylcyclohexanol | 2.50 |
| Cis-Jasmone at 10% | 0.50 |
| Linalool | 6.00 |
| Lyral | 1.00 |
| Methyl cedryl ketone | 2.00 |
| Methylisoeugenol | 2.00 |
| Amyl salicylate | 2.00 |
| Benzyl salicylate | 7.50 |
| Terpineol | 3.50 |
| Vetiverol | 2.00 |
| Ylang-ylang | 3.00 |
| Cis-isoambrettolide (isomer purity of 99.5%) | 2.00 |
| | 79.00 |

The cis-isoambrettolide gives the note more development, a rounder, more sophisticated note and musky and powdery long-lasting effect.

EXAMPLE 2

It is also used in a fresh, citrugy, woody, ambery note for a unisex or masculine eau de toilette according to the formula below: (parts by weight)

| | |
|---|---|
| Acetal Bois 12 | 7.40 |
| Cedrenyl acetate | 1.20 |
| Isobornyl acetate | 2.50 |
| Linalyl acetate | 3.00 |
| Styrallyl acetate | 0.50 |
| Adoxal at 10% | 0.25 |
| Mandarin aldehyde at 10% | 0.25 |
| Allyl amyl glycolat | 0.60 |
| Ambrox DL at 10% | 2.50 |
| Calone 161 at 10% | 0.30 |
| L-Carvone at 10% | 1.50 |
| Lemon oil | 8.40 |
| Cyclogalbanate | 0.40 |
| Alpha Damascone at 10% | 4.00 |
| Citral diethyl acetal | 1.20 |
| Dihydromyrcenol | 2.70 |
| Dimethylcyclohexenecarbaldehyde at 10% | 1.80 |
| Ethyllinalool | 8.00 |
| Ethyltrimethylcyclopentenyl at 10% | 1.20 |
| Evernyl | 0.30 |
| Hedione | 10.00 |
| Helional | 1.70 |
| Hydroxycitronellal | 0.70 |
| Jessemal at 10% | 2.00 |
| Lavandin oil | 3.00 |
| Mandarin oil | 1.00 |
| Mentha citrata oil | 0.10 |
| Gamma Methylionone | 0.50 |
| Orange oil | 5.00 |
| Cis-Isoambrettolide (isomer purity of 99.5%) | 6.00 |
| | 78.00 |

The cis-isoambrettolide gives a musky character and develops the entire note and most particularly its citrus aspect, its long-lastingness and its freshness.

These same results of development of the note, of its long-lastingness and the fresh notes with a more sophisticated effect, are found in the fragrance compounds intended mainly for cosmetic preparations, for toiletries, for shampoos and hair products.

EXAMPLE 3

The use of cis-isoambrettolide is also very efficient in fragrance compounds intended for soaps, detergents, household cleaners and fabric softeners.

Thus, in the formula below, with a fresh, long-lasting note and a fruity aspect: (parts by weight)

| | |
|---|---|
| Para-tert-butylcyclohexyl acetate | 6.00 |
| Dimethylbenzylcarbinyl acetate | 0.70 |
| Cis-3-Hexenyl acetate | 0.05 |
| Styrallyl acetate | 2.50 |
| Verdyl acetate | 4.00 |
| Phenylethyl alcohol | 1.00 |
| Hexylcinnamic aldehyde | 10.00 |
| Algix at 20% | 6.00 |
| Ambroxan at 10% | 1.00 |
| Methylmethoxyphenylpropanal | 0.60 |
| Cerinthol | 1.00 |
| Cetone alpha | 2.00 |
| Dihydroionone Delta | 4.00 |
| Dihydromyrcenol | 7.30 |
| Eugenol | 0.20 |
| Floropal | 1.80 |
| Geraniol | 1.00 |
| Geranyl nitrile | 0.50 |
| Hedione | 10.00 |
| Cis-3-Hexenol | 0.15 |
| Menthol | 0.30 |
| Methyl cedryl ketone | 10.00 |
| Gamma Methylionone | 4.60 |
| Nonadienal 2–6 DEA at 1% | 1.00 |
| Orange oil | 4.50 |
| Cis-3-Hexenyl salicylate | 1.00 |
| Undecalactone | 0.80 |
| Cis-Isoambrettolide (isomer purity of 99.5%) | 10.00 |
| | 92.00 |

The same compositions as in Examples 1–3 were prepared with the trans isomer (isomer purity of 98.5%) used instead of the cis isomer of the isoambrettolide.

The olfactory effects between the compositions of Examples 1 to 3 have been compared by two perfumers. The comparative results are as follows:

Compositions of Examples 1 to 3 Tested by the First Perfumer

Example 1
With Trans-isoambrettolide:
The trans-isoambrettolide brings a floral bouquet, mainly ylang, on a round musky note.
With Cis-isoambrettolide:
The cis-isoambre ttolide develops the green notes and the fresh notes of the composition.

Example 2
With Trans-isoambrettolide:
The note is fresh, floral, fruity, woody and slightly "acidic".
With Cis-isoambrettolide:
The note is fresh but not "acidic", as the cis-isoambrettolide develops the green notes and rounds up the notes of the background.

Example 3
With Trans-isoambrettolide:
The trans-isoambrettolide develops the fresh, green, slightly aromatic notes. The woody notes are earthy.
With Cis-isoambrettolide:

The cis-isoambrettolide rounds the floral note and develops the hesperidic, green, fruity fresh notes. The dry out is softer.

Conclusion:

The cis-isoambrettolide and the trans-isoambrettolide have very different olfactory effects in the top-notes as well as on the floral notes of the heart and on the notes of the background which may be more woody, more musky, more round depending the ambrettolide used. Although the two products are isomers, they bring different notes and different development to the compositions.

Compositions of Examples 1 to 3 Tested by the Second Perfumer

Example 1

With Trans-isoambrettolide:

The trans-isoambrettolide does not act on the freshness, gives a clean musky dry out and does not bind the spicy notes.

With Cis-isoambrettolide:

The cis-isoambrettolide develops the top notes, gives an aspect of leathery-suede note, brings a warm note and rounds the whole compound. The musky note is more round and natural.

Example 2

With Trans-isoambrettolide:

The fruity notes are quite noticeable in the top notes. The composition lacks softness.

With Cis-isoambrettolide:

The cis-isoambrettolide develops the hesperidic freshness and the fruity notes, rounds the fruity and green notes and brings a soft, natural background.

Example 3

With Trans-isoambrettolide:

An acid green odor is excessive in the top note.

With Cis-isoambrettolide:

The cis-isoambrettolide develops the top note, binds the whole composition, bring a musky background more natural and covers the "detergent" note.

Conclusion:

The two products bring very different olfactory results. The cis-isoambrettolide brings an expansion of the top notes and the development and tenacity of the whole notes of the composition.

It should be clear that similar tests carried out with industrially manufactured cis-isoambrettolide having an isomeric purity lower than 99.5%, for instance of about 90 or 95%, would give similar results, if the corresponding impurities have no particular detrimental olfactory effect.

These results could in general be identical after adapting the content of cis-isoambrettolide according to the isomer purity thereof.

The different compositions tested point out the fact that the olfactory effects given by the cis-isoambrettolide on one hand and by the trans-isoambrettolide on the other hand, are completely different, as well on the top notes as on the notes of the background.

The high degree of isomer purity of the cis-isoambrettolide provides a new, unforeseeable and surprising olfactory effect, this advantage being combined with the advantage of being much more powerful than trans-isoambrettolide in olfactory terms.

The cis-isoambrettolide develops the fresh note of this composition throughout the evaporation of the product and its long-lastingness and substantivity and develops a musky note.

Such fragrance composition including the cis-isoambrettolide according to the present invention can be used in different kinds of products, for instance such as perfumes, toilets waters, cosmetic preparations, toiletries, shampoos, hair products, soaps, candles, air fresheners, detergents, textile softeners and household products.

Although the present description of the invention has been made with reference to specific embodiments, it is clear that various minor procedural modifications, which are within the immediate scope of a person skilled in the art, can be made without, however, departing from the scope of the invention as described and claimed.

What is claimed is:

1. A substantially pure cis-isoambrettolide having the formula:

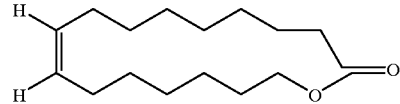

wherein the compound has a geometrical isomer purity of at least 90%.

2. The compound of claim 1 having a geometrical isomer purity of at least 95%.

3. The compound of claim 2 having a geometrical isomer purity of at least 97%.

4. The compound of claim 3 having a geometrical isomer purity of at least 99.5%.

5. A fragrance composition containing a fragrance enhancing amount of the compound of claim 1.

6. The composition of claim 5 wherein said compound has a geometrical isomer purity of at least 95%.

7. The composition of claim 6 wherein said compound has a geometrical isomer purity of at least 97%.

8. The composition of claim 7 wherein said compound has a geometrical isomer purity of at least 99.5%.

9. The composition of claim 6 wherein said fragrance composition comprises a product selected from the group consisting of perfumes, toilets waters, cosmetic preparations, toiletries, shampoos, hair products, soaps, candles, air fresheners, detergents, textile softeners and household products.

10. The composition of claim 5 wherein said compound is present in said composition at a level of at least about 0.01 wt %.

11. The composition of claim 10 wherein said compound is present in said composition at a level of from about 0.15 to 15 wt %.

* * * * *